(12) United States Patent
Durschang et al.

(10) Patent No.: US 9,125,812 B2
(45) Date of Patent: Sep. 8, 2015

(54) LITHIUM SILICATE GLASS CERAMIC, METHOD FOR PRODUCTION THEREOF AND USE THEREOF

(75) Inventors: Bernhard Durschang, Rottendorf (DE); Jörn Probst, Kürnach (DE); Norbert Thiel, Bad Säckingen (DE); Michael Gödiker, Säckingen (DE); Markus Vollmann, Gelnhausen (DE); Udo Schusser, Alzenau (DE)

(73) Assignees: FRAUNHOFER-GESELLSCHAFT ZUR FÖRDERUNG DER ANGEWANDTEN FORSCHUNG E.V., München (DE); VITA ZAHNFABRIK H. RAUTER GMBH & CO. KG, Bad Säckingen (DE); DEGUDENT GMBH, Hanau (DE)

( * ) Notice: Subject to any disclaimer, the term of this patent is extended or adjusted under 35 U.S.C. 154(b) by 127 days.

(21) Appl. No.: 13/880,894

(22) PCT Filed: Jun. 22, 2011

(86) PCT No.: PCT/EP2011/003091
§ 371 (c)(1),
(2), (4) Date: Jul. 24, 2013

(87) PCT Pub. No.: WO2012/059143
PCT Pub. Date: May 10, 2012

(65) Prior Publication Data
US 2013/0295523 A1    Nov. 7, 2013

(30) Foreign Application Priority Data

Nov. 2, 2010 (DE) .......................... 10 2010 050 275

(51) Int. Cl.
| | | |
|---|---|---|
| *A61K 6/027* | (2006.01) |
| *C03C 10/04* | (2006.01) |
| *C03C 3/097* | (2006.01) |
| *C03C 10/00* | (2006.01) |
| *A61C 5/10* | (2006.01) |
| *A61C 13/00* | (2006.01) |
| *A61K 6/02* | (2006.01) |
| *A61K 6/033* | (2006.01) |
| *A61K 6/04* | (2006.01) |

(52) U.S. Cl.
CPC ................. *A61K 6/0273* (2013.01); *A61C 5/10* (2013.01); *A61C 13/0003* (2013.01); *A61K 6/024* (2013.01); *A61K 6/025* (2013.01); *A61K 6/0215* (2013.01); *A61K 6/0235* (2013.01); *A61K 6/0245* (2013.01); *A61K 6/0255* (2013.01); *A61K 6/0276* (2013.01); *A61K 6/033* (2013.01); *A61K 6/043* (2013.01); *A61K 6/046* (2013.01); *C03C 3/097* (2013.01); *C03C 10/0027* (2013.01)

(58) Field of Classification Search
CPC .. A61K 6/0205; A61K 6/024; C03C 10/0009; C03C 10/0027
USPC ............................................................ 501/5
See application file for complete search history.

(56) References Cited

U.S. PATENT DOCUMENTS

| | | | |
|---|---|---|---|
| 2,684,911 A | 7/1954 | Stookey | |
| 3,238,085 A | 3/1966 | Hayami et al. | |
| 4,515,634 A | 5/1985 | Wu et al. | |
| 5,507,981 A | 4/1996 | Petticrew | |
| 5,698,482 A | 12/1997 | Frank et al. | |
| 5,925,180 A | 7/1999 | Frank et al. | |
| 6,420,288 B2 * | 7/2002 | Schweiger et al. ............... 501/7 |
| 6,426,311 B1 | 7/2002 | Goto et al. | |
| 6,524,982 B1 | 2/2003 | Nagata et al. | |
| 7,166,548 B2 | 1/2007 | Apel et al. | |
| 7,452,836 B2 | 11/2008 | Apel et al. | |
| 7,867,930 B2 | 1/2011 | Apel et al. | |
| 7,867,931 B2 | 1/2011 | Apel et al. | |
| 7,867,933 B2 | 1/2011 | Apel et al. | |
| 7,871,948 B2 | 1/2011 | Apel et al. | |
| 7,993,137 B2 | 8/2011 | Apel et al. | |
| 8,162,664 B2 | 4/2012 | Apel et al. | |
| 8,536,078 B2 | 9/2013 | Ritzberger et al. | |
| 8,546,280 B2 | 10/2013 | Apel et al. | |
| 8,557,150 B2 | 10/2013 | Ritzberger et al. | |

(Continued)

FOREIGN PATENT DOCUMENTS

| | | |
|---|---|---|
| CA | 2213390 A1 | 3/1998 |
| CA | 2252660 A1 | 5/1999 |

(Continued)

OTHER PUBLICATIONS

Borom et al., "Strength and Microstructure in Lithium Disilicate Glass-Ceramics", *Journal of the American Ceramic Society*, vol. 58, No. 9-10, pp. 385-391 (1975).
De Oliveira et al., "Sintering and Crystallization of a Glass Powder in the $Li_2O$—$ZrO_2$—$SiO_2$ System," *Communications of the American Ceramic Society*, vol. 81, No. 3, pp. 777-780 (1998).
Montedo et al. "Low Thermal Expansion Sintered LZSA Glass-Ceramics," *American Ceramic Society Bulletin*, vol. 87. No. 7, pp. 34-40 (2008).
Stookey, "Chemical Machining of Photosensitive Glass", *Industrial and Engineering Chemistry*, 45, pp. 115-118 (1993).
Von Clausbruch et al., "Crystallization, Microstructure and Properties of Selected Glasses and Glass-Ceramics in the $SiO_2$—$Li_2O$—ZnO—$K_2O$—$P_2O_5$ System," *DGG Journal*, vol. 1, No. 1, pp. 41-49 (2002).
European Patent Office, International Search Report in International Application No. PCT/EP2011/003091 (Sep. 20, 2011).

(Continued)

*Primary Examiner* — Karl Group
(74) *Attorney, Agent, or Firm* — Leydig, Voit & Mayer, Ltd.

(57) ABSTRACT

The invention relates to glass ceramics based on the lithium metasilicate system ($Li_2OSiO_2(Li_2SiO_3)$), which are mechanically processible in a simple manner in an intermediate stage of the crystallization and, after complete crystallization, represent a high-strength, highly translucent and chemically stable glass ceramic.

16 Claims, 3 Drawing Sheets

(56) References Cited

U.S. PATENT DOCUMENTS

| | | | |
|---|---|---|---|
| 8,759,237 B2 | 6/2014 | Ritzberger et al. | |
| 8,778,075 B2 | 7/2014 | Ritzberger et al. | |
| 8,956,987 B2 * | 2/2015 | Durschang et al. | 501/5 |
| 2002/0010063 A1 | 1/2002 | Schweiger et al. | |
| 2005/0209082 A1 | 9/2005 | Apel et al. | |
| 2007/0042889 A1 | 2/2007 | Apel et al. | |
| 2009/0038344 A1 | 2/2009 | Apel et al. | |
| 2009/0038508 A1 | 2/2009 | Apel et al. | |
| 2009/0042713 A1 | 2/2009 | Apel et al. | |
| 2009/0042714 A1 | 2/2009 | Apel et al. | |
| 2009/0256274 A1 | 10/2009 | Castillo | |
| 2010/0083706 A1 | 4/2010 | Castillo | |
| 2011/0030423 A1 | 2/2011 | Johannes et al. | |
| 2011/0059836 A1 | 3/2011 | Apel et al. | |
| 2011/0252831 A1 | 10/2011 | Apel et al. | |
| 2011/0256409 A1 | 10/2011 | Ritzberger et al. | |
| 2011/0257000 A1 | 10/2011 | Ritzberger et al. | |
| 2011/0259053 A1 | 10/2011 | Apel et al. | |
| 2012/0248642 A1 | 10/2012 | Ritzberger et al. | |
| 2012/0309607 A1 | 12/2012 | Durschang et al. | |
| 2013/0296156 A1 | 11/2013 | Apel et al. | |
| 2013/0323404 A1 | 12/2013 | Ritzberger et al. | |
| 2014/0000314 A1 | 1/2014 | Ritzberger et al. | |
| 2014/0200129 A1 | 7/2014 | Durschang et al. | |
| 2014/0249016 A1 | 9/2014 | Durschang et al. | |
| 2014/0252272 A1 | 9/2014 | Durschang et al. | |
| 2014/0335473 A1 | 11/2014 | Ritzberger et al. | |

FOREIGN PATENT DOCUMENTS

| | | |
|---|---|---|
| CN | 1306946 A | 8/2001 |
| DE | 14 21 886 A1 | 6/1969 |
| DE | 24 51 121 A1 | 5/1975 |
| DE | 10 2004 013455 B3 | 9/2005 |
| DE | 10 2005 028637 A1 | 12/2006 |
| DE | 10 2007 011337 A1 | 9/2008 |
| EP | 0 536 572 A1 | 4/1993 |
| EP | 0 536 479 B1 | 9/1995 |
| EP | 0 690 031 A1 | 1/1996 |
| EP | 0 827 941 A1 | 3/1998 |
| EP | 0 916 625 A1 | 5/1999 |
| EP | 1 505 041 A1 | 2/2005 |
| EP | 1 688 397 A1 | 8/2006 |
| EP | 2 305 614 A2 | 4/2011 |
| EP | 2 377 831 A1 | 10/2011 |
| FR | 2 655 264 A | 6/1991 |
| JP | S39-007912 A | 5/1964 |
| JP | S58-120539 A | 7/1983 |
| JP | H08-040744 A | 2/1996 |
| JP | H10-101409 A | 4/1998 |
| JP | H11-314938 A | 11/1999 |
| JP | 2001-019468 A | 1/2001 |
| JP | 2005-053776 A | 3/2005 |
| JP | 2005-062832 A | 3/2005 |
| JP | 2006-219367 A | 8/2006 |
| JP | 2011-225441 A | 11/2011 |
| JP | 2013-515659 A | 5/2013 |
| WO | WO 95/32678 A2 | 12/1995 |
| WO | WO 2009/126317 A1 | 10/2009 |
| WO | WO 2011/076422 A1 | 6/2011 |
| WO | WO 2012/175450 A1 | 12/2012 |
| WO | WO 2012/175615 A1 | 12/2012 |

OTHER PUBLICATIONS

European Patent Office, International Preliminary Report on Patentability in International Application No. PCT/EP2011/003091 (Jan. 4, 2013).

European Patent Office, Third Party Observation in International Application No. PCT/EP2011/003091 (Nov. 14, 2012).

Japanese Patent Office, Third Party Observation in Japanese Patent Application No. 2013-535284 (Jul. 25, 2014).

European Patent Office, Communication Pursuant to Rule 114(2) EPC—Third Party Observation in European Patent Application No. 11727924.0 (Jul. 16, 2014).

Japanese Patent Office, Notice of Rejection in Japanese Patent Application No. 2013-535284 (Nov. 19, 2014).

State Intellectual Property Office of the People's Republic of China, First Office Action in Chinese Patent Application No. 201180052923.6 (Dec. 29, 2014).

* cited by examiner

LITHIUM SILICATE GLASS CERAMIC, METHOD FOR PRODUCTION THEREOF AND USE THEREOF

CROSS-REFERENCE TO RELATED APPLICATIONS

This patent application is the U.S. national phase of International Application No. PCT/EP2011/003091, filed Jun. 22, 2011, which claims the benefit of German Patent Application No. 10 2010 050 275.8, filed Nov. 2, 2010, the disclosures of which are incorporated by reference.

The invention relates to glass ceramics based on the lithium metasilicate system ($Li_2O.SiO_2(Li_2SiO_3)$), which are mechanically processible in a simple manner in an intermediate stage of the crystallization and, after complete crystallization, represent a high-strength, highly translucent and chemically stable glass ceramic.

In the lithium oxide-silicon dioxide system, lithium disilicate ($Li_2O.2SiO_2(Li_2Si_2O_5)$)-glass ceramics are well known from the literature and several patents are based on this glass ceramic system. For example, in EP-B-536 479, self-glazed lithium disilicate glass ceramic objects are thus described for the production of tableware and, in EP-B-536 572, lithium disilicate glass ceramics which can be used by scattering a fine-particle coloured glass onto the surface thereof as cladding elements for building purposes, A main focus of the patented lithium disilicate glass ceramics resides in dental applications. The lithium disilicate system is very suitable here for the production of CAD/CAM-processible glass ceramics since the crystallization is effected here via the lithium metasilicate phase (see S. D. Stookey: "Chemical Machining of Photosensitive Glass", Ind. Eng. Chem., 45, 115-118 (1993) and S. D. Stookey: "Photosensitively Opacifiable Glass" U.S. Pat. No. 2,684,911 (1954)). These lithium metasilicate glass ceramics have such low strengths in this intermediate stage that they can be readily processed by means of CAD/CAM (M.-P. Borom, A. M. Turkalo, R. H. Doremus: "Strength and Microstructure in Lithium Disilicate Glass Ceramics", J. Am. Ceram. Soc., 58, No. 9-10, 385-391 (1975) and M.-P. Borom, A. M. Turkalo, R. H. Doremus: "Verfahren zum Herstellen von Glaskeramiken" (Method for the production of glass ceramics) DE-A-24 51 121 (1974)). Only by the subsequent conversion to form lithium disilicate in a second crystallization stage are dental materials with high strengths achieved.

This principle is exploited in order to produce firstly a glass ceramic, in a two-stage crystallization process, which glass ceramic can be readily processed mechanically, e.g. by means of CAD/CAM processes, and in order to process this subsequently in a second crystallization stage to form dental glass ceramic. This method is suitable in order to be able to use dental restorations according to the so-called chair-side method. In this method, an individually adapted crown/onlay/inlay is milled out of a glass ceramic block after the first crystallization stage by means of CAD/CAM, in the dental practice this is subjected to the second crystallization stage in a special oven and used directly in the first and only dentist's visit for the patient (DE 10 2005 028 637). An application by the dental technician in the pressing method or in mechanical processing with subsequent characterisation or individualisation whilst taking into account suitable paints or layer ceramics can also be effected.

Starting herefrom, it was the object of the present invention to provide glass ceramics which have improved strength values and also improved translucence and chemical resistance.

This object is achieved by the features of the lithium silicate glasses or glass ceramics, the method for producing a dental restoration and shaped dental restoration described herein, and the advantageous developments thereof. Uses of the lithium silicate glasses or glass ceramics are also described.

Within the scope of the present invention, glass compositions were developed in the basic system $SiO_2$—$Li_2O$—$ZrO_2$, which have lithium metasilicate as only or as main crystal phase (>50%). %). Hereby, zirconia acts as a stabilizer of the residual glassy phase and can be completely or partially replaced by oxides of Hafnium, Germanium, Cerium, Lanthanum, Yttrium, Titanium and zinc.

Surprisingly, it was shown that lithium metasilicate glass ceramics which have excellent strength values, exceptional translucence and very good chemical resistances can be produced in this system.

It was shown in addition that up to 20% by weight of $ZrO_2$ or other stabilizers can be incorporated in the glass without the structure being significantly influenced. Contrary to all expectations, the $ZrO_2$ or other stabilizers does not hereby crystallise as a separate crystal phase but remains completely or extensively in the amorphous residual glass phase. Because of the high proportion of $ZrO_2$ or other stabilizers, the mechanical and chemical resistances are hugely improved in this amorphous phase, which also leads to improved properties in the entire dental glass ceramic (crystal phase(s) and residual glass phase), such as for example final strength and acid solubility.

The method is also suitable for a two-stage production process from the initial glass, a partial crystallization of the lithium metasilicate being effected in the first processing stage, which enables good CAD/CAM processing. In the second processing stage, an increase in the crystal phase proportion (primary lithium metasilicate) is effected, which leads to the high strength values. The most important cause of the surprisingly high strengths in the lithium metasilicate system is hereby ascribed to the high zirconium oxide or other stabilizers proportion (>8 MA).

High translucence is ensured via the low crystallite size in the glass ceramics. In addition, good chemical stability is ensured by the high zirconium oxide proportion in the glass phase and the enriched amount of $SiO_2$ in the residual glassy phase compared to lithiumdisilicate-glass-ceramics (Lithiumdisilicate=Lithiummetasilicate+$SiO_2$).

According to the invention, lithium silicate glasses or glass ceramics with the following composition are provided:
50 to 75 wt-% $SiO_2$,
10 to 25 wt-% $Li_2O$,
5 to 30 wt-% of a stabilizer selected from the group consisting of the oxides of Zr, Hf, Ge, La, Y, Ce, Ti, Zn or its mixtures,
0 to 8 wt-% $K_2O$ and/or $Na_2O$,
0 to 8 wt-% $Al_2O_3$, and
0 to 15 wt-% additives.

Preferably, the glasses or glass ceramics have the following composition:
50 to 75 wt-% $SiO_2$,
10 to 25 wt-% $Li_2O$,
5 to 30 wt-% of a stabilizer selected from the group consisting of $ZrO_2$ and/or $HfO_2$,
0 to 8 wt-% $K_2O$ and/or $Na_2O$,
0 to 8 wt-% $Al_2O_3$, and
0 to 15 wt-% additives.

More preferably, the glasses or glass ceramics have the following composition:
50 to 70 wt-% $SiO_2$,
15 to 22 wt-% $Li_2O$, 8 to 20 wt-% of a stabilizer selected from the group consisting of the oxides of Zr, Hf, Ge, La, Y, Ce, Ti, Zn or its mixtures,
0.1 to 4 wt-% $K_2O$ and/or $Na_2O$,
0.1 to 4 wt-% $Al_2O_3$, and
2 to 8 wt-% additives.

In a preferred embodiment, the glasses or glass ceramics have the following composition:
50 to 70 wt-% $SiO_2$,
15 to 22 wt-% $Li_2O$,
8 to 20 wt-% of a stabilizer selected from the group consisting of $ZrO_2$ and/or $HfO_2$,
0.1 to 4 wt-% $K_2O$ and/or $Na_2O$,
0.1 to 4 wt-% $Al_2O_3$, and
2 to 8 wt-% additives.

In a further preferred embodiment, the glasses or glass ceramics have the following composition:
50 to 64 wt-% $SiO_2$,
17 to 20 wt-% $Li_2O$,
8 to 20 wt-% of a stabilizer selected from the group consisting of $ZrO_2$ and/or $HfO_2$,
1 to 3 wt-% $K_2O$ and/or $Na_2O$,
1 to 3 wt-% $Al_2O_3$, and
4 to 6 wt-% additives.

In a further preferred embodiment the glasses or glass ceramics have the following composition:
55 to 64% by weight of $SiO_2$,
10 to 20% by weight of $Li_2O$,
8 to 20% by weight of a stabilizer selected from the group consisting of $ZrO_2$, $HfO_2$ or mixtures hereof,
0 to 5% by weight of $K_2O$ and/or $Na_2O$,
0.1 to 5% by weight of $Al_2O_3$ and also 0 to 10% by weight of additives.

In a further preferred embodiment the glasses or glass ceramics have the following composition:
55 to 60% by weight of $SiO_2$,
10 to 20% by weight of $Li_2O$,
8 to 20% by weight of a stabilizer selected from the group consisting of $ZrO_2$, $HfO_2$ or mixtures hereof,
0 to 5% by weight of $K_2O$ and/or $Na_2O$,
0.1 to 5% by weight of $Al_2O_3$ and also 0 to 10% by weight of additives.

Furthermore, a glass or a glass ceramic with the following composition is preferred:
55 to 64% by weight of $SiO_2$,
10 to 20% by weight of $Li_2O$,
10 to 20% by weight of a stabilizer selected from the group consisting of $ZrO_2$, $HfO_2$ or mixtures hereof,
0 to 5% by weight of $K_2O$ and/or $Na_2O$,
0.1 to 5% by weight of $Al_2O_3$ and also
0 to 10% by weight of additives.

A further preferred composition comprises
55 to 60% by weight of $SiO_2$,
10 to 20% by weight of $Li_2O$,
10 to 20% by weight of a stabilizer selected from the group consisting of $ZrO_2$, $HfO_2$ or mixtures hereof,
0 to 5% by weight of $K_2O$ and/or $Na_2O$,
0.1 to 5% by weight of $Al_2O_3$ and also
0 to 10% by weight of additives.

The stabilizer is preferably $ZrO_2$ and/or $HfO_2$. Preferably, the stabilizer is essentially present in an amorphous state.

There may be contained as additives, components selected from the group consisting of nucleation agents, fluorescent agents, dyes, in particular glass-colouring oxides, coloured pigments and mixtures thereof, in the glass or in the glass ceramic.

As for all glasses and glass-ceramics, some components have effects on several properties. For example, titania can act as nucleation and colouring agent. Most of the rare earth metal oxides show effects on colour and fluorescence. Some components can be simultaneously amorphous, incorporated in crystalline phases and build own crystalline phases.

The nucleating agents are preferably selected from the group consisting of phosphorous oxide, titanium oxide, tin oxide, mixtures thereof, and noble metals, preferably in an amount of 1 to 10 wt-%, more preferably 2 to 8 wt-% and most preferably 4 to 8 wt-%.

The fluorescent agents are preferably selected from the group consisting of oxides of bismuth, rare earth elements as neodymium, praseodymium, samarium, erbium, and europium, and mixtures thereof, preferably in an amount of 0.1 to 5 wt-%, more preferably 0.5 to 4 wt-% and most preferably 1 to 3 wt-%.

The glass colouring oxides are preferably selected from the group of oxides of iron, titanium, cerium, copper, chromium, cobalt, nickel, manganese, selenium, silver, indium, gold, vanadium, rare earth elements as neodymium, praseodymium, samarium, europium, terbium, dysprosium, holmium, erbium, yttrium, and mixtures thereof, preferably in an amount of 0.1 to 6 wt-%, more preferably 0.5 to 5 wt-% and most preferably 1 to 4 wt-%.

The coloured pigments can be doped spinels, which are comprised preferably in an amount of 0.1 to 6 wt-%, more preferably 0.5 to 5 wt-% and most preferably 1 to 4 wt-%.

Further additives are preferably selected from the group consisting of boron oxide, phosphorus oxide, fluorine, sodium oxide, barium oxide, strontium oxide, magnesium oxide, zinc oxide, calcium oxide, yttrium oxide, titanium oxide, niobium oxide, tantalum oxide, lanthanum oxide and mixtures thereof, which are comprised preferably in an amount of 0.1 to 5 wt-%.

According to the invention, a method for the above-described lithium silicate glasses or glass ceramics and a method for producing a dental restoration comprising the above-described lithium silicate glass or glass ceramic is likewise provided, wherein a) an glass is provided as starting material which comprises the components of the glass ceramic,
b) the glass is subjected to a first heat treatment for producing a glass ceramic which comprises lithium metasilicate as exclusive or main crystal phase,
c) the glass ceramic of b) is subjected to a second heat treatment, wherein further metasilicate is segregated from the glass phase. The lithium metasilicate is present as main crystal phase.

The first heat treatment is thereby effected preferably at a temperature of 620° C. to 950° C. over a period of time of 1 to 200 minutes. It is particularly preferred to implement the first heat treatment at temperatures of 650° C. to 750° C. over a period of time of 10 to 60 minutes.

The further crystallization of the lithium metasilicate takes place preferably at temperatures between 800° C. and 1,040° C. over a period of time of 5 to 200 minutes, particularly preferred between 800° C. and 870° C. over a period of time of 5 to 30 minutes.

The lithium silicate glasses or glass ceramics according to the invention are used as dental material or as component of a dental material.

According to the invention, a shaped dental product which comprises the previously-described lithium silicate glass or the lithium silicate glass ceramic is likewise provided. The shaped dental products are thereby present in particular in the form of an inlay, an onlay, a bridge, an abutment, a facing, a veneer, a facet, a crown, a partial crown, a framework or a coping.

The lithium silicate glasses or glass ceramics with the following compositions are further aspects of the present invention:

| Composition 1 | |
|---|---|
| $SiO_2$ | 50 to 75 wt-% |
| $Li_2O$ | 10 to 25 wt-% |
| $ZrO_2$ | 5 to 30 wt-% |
| $Al_2O_3$ | 0 to 8 wt-% |
| $K_2O$ | 0 to 8 wt-% |
| additives | 0 to 15 wt-% |

| Composition 2 | |
|---|---|
| $SiO_2$ | 50 to 64 wt-% |
| $Li_2O$ | 10 to 25 wt-% |
| $ZrO_2$ | 5 to 30 wt-% |
| $Al_2O_3$ | 0 to 8 wt-% |
| $K_2O$ | 0 to 8 wt-% |
| additives | 0 to 15 wt-% |

| Composition 3 | |
|---|---|
| $SiO_2$ | 55 to 60 wt-% |
| $Li_2O$ | 10 to 25 wt-% |
| $ZrO_2$ | 5 to 30 wt-% |
| $Al_2O_3$ | 0 to 8 wt-% |
| $K_2O$ | 0 to 8 wt-% |
| additives | 0 to 15 wt-% |

| Composition 4 | |
|---|---|
| $SiO_2$ | 50 to 75 wt-% |
| $Li_2O$ | 15 to 22 wt-% |
| $ZrO_2$ | 5 to 30 wt-% |
| $Al_2O_3$ | 0 to 8 wt-% |
| $K_2O$ | 0 to 8 wt-% |
| additives | 0 to 15 wt-% |

| Composition 5 | |
|---|---|
| $SiO_2$ | 50 to 75 wt-% |
| $Li_2O$ | 17 to 20 wt-% |
| $ZrO_2$ | 5 to 30 wt-% |
| $Al_2O_3$ | 0 to 8 wt-% |
| $K_2O$ | 0 to 8 wt-% |
| additives | 0 to 15 wt-% |

| Composition 6 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 7 | |
|---|---|
| $SiO_2$ | 50 to 75 wt-% |
| $Li_2O$ | 10 to 25 wt-% |
| $ZrO_2$ | 10 to 15 wt-% |
| $Al_2O_3$ | 0 to 8 wt-% |
| $K_2O$ | 0 to 8 wt-% |
| additives | 0 to 15 wt-% |

| Composition 8 | |
|---|---|
| $SiO_2$ | 50 to 75 wt-% |
| $Li_2O$ | 10 to 25 wt-% |
| $ZrO_2$ | 5 to 30 wt-% |
| $Al_2O_3$ | 0.1 to 5 wt-% |
| $K_2O$ | 0 to 8 wt-% |
| additives | 0 to 15 wt-% |

| Composition 9 | |
|---|---|
| $SiO_2$ | 50 to 75 wt-% |
| $Li_2O$ | 10 to 25 wt-% |
| $ZrO_2$ | 5 to 30 wt-% |
| $Al_2O_3$ | 1 to 3 wt-% |
| $K_2O$ | 0 to 8 wt-% |
| additives | 0 to 15 wt-% |

| Composition 10 | |
|---|---|
| $SiO_2$ | 50 to 75 wt-% |
| $Li_2O$ | 10 to 25 wt-% |
| $ZrO_2$ | 5 to 30 wt-% |
| $Al_2O_3$ | 0 to 8 wt-% |
| $K_2O$ | 0.1 to 5 wt-% |
| additives | 0 to 15 wt-% |

| Composition 11 | |
|---|---|
| $SiO_2$ | 50 to 75 w-% |
| $Li_2O$ | 10 to 25 wt-% |
| $ZrO_2$ | 5 to 30 wt-% |
| $Al_2O_3$ | 0 to 8 wt-% |
| $K_2O$ | 1 to 3 wt-% |
| additives | 0 to 15 wt-% |

| Composition 12 | |
|---|---|
| $SiO_2$ | 50 to 75 wt-% |
| $Li_2O$ | 10 to 25 wt-% |
| $ZrO_2$ | 5 to 30 wt-% |
| $Al_2O_3$ | 0 to 8 wt-% |
| $K_2O$ | 0 to 8 wt-% |
| additives | 1 to 10 wt-% |

| Composition 13 | |
|---|---|
| $SiO_2$ | 50 to 75 wt-% |
| $Li_2O$ | 10 to 25 wt-% |
| $ZrO_2$ | 5 to 30 wt-% |
| $Al_2O_3$ | 0 to 8 wt-% |
| $K_2O$ | 0 to 8 wt-% |
| additives | 2 to 8 wt-% |

| Composition 14 | |
|---|---|
| $SiO_2$ | 50 to 75 wt-% |
| $Li_2O$ | 10 to 25 wt-% |
| $ZrO_2$ | 5 to 30 wt-% |
| $Al_2O_3$ | 0 to 8 wt-% |
| $K_2O$ | 0 to 8 wt-% |
| additives | 4 to 6 wt-% |

| Composition 15 | |
|---|---|
| $SiO_2$ | 50 to 75 wt-% |
| $Li_2O$ | 10 to 25 wt-% |
| $ZrO_2$ | 5 to 30 wt-% |
| $P_2O_5$ | 1 to 10 wt-% |
| $Al_2O_3$ | 0 to 8 wt-% |
| $K_2O$ | 0 to 8 wt-% |
| additives | 0 to 5 wt-% |

| Composition 16 | |
|---|---|
| $SiO_2$ | 50 to 75 wt-% |
| $Li_2O$ | 10 to 25 wt-% |
| $ZrO_2$ | 5 to 30 wt-% |
| $P_2O_5$ | 2 to 8 wt-% |
| $Al_2O_3$ | 0 to 8 wt-% |
| $K_2O$ | 0 to 8 wt-% |
| additives | 0 to 7 wt-% |

| Composition 17 | |
|---|---|
| $SiO_2$ | 50 to 75 wt-% |
| $Li_2O$ | 10 to 25 wt-% |
| $ZrO_2$ | 5 to 30 wt-% |
| $P_2O_5$ | 4 to 6 wt-% |
| $Al_2O_3$ | 0 to 8 wt-% |
| $K_2O$ | 0 to 8 wt-% |
| additives | 0 to 9 wt-% |

| Composition 18 | |
|---|---|
| $SiO_2$ | 55 to 64 wt-% |
| $Li_2O$ | 10 to 25 wt-% |
| $ZrO_2$ | 5 to 30 wt-% |
| $P_2O_5$ | 1 to 10 wt-% |
| $Al_2O_3$ | 0 to 8 wt-% |
| $K_2O$ | 0 to 8 wt-% |
| additives | 0 to 5 wt-% |

-continued

| Composition 19 | |
|---|---|
| SiO$_2$ | 55 to 64 wt-% |
| Li$_2$O | 15 to 22 wt-% |
| ZrO$_2$ | 5 to 30 wt-% |
| P$_2$O$_5$ | 1 to 10 wt-% |
| Al$_2$O$_3$ | 0 to 8 wt-% |
| K$_2$O | 0 to 8 wt-% |
| additives | 0 to 5 wt-% |

| Composition 20 | |
|---|---|
| SiO$_2$ | 55 to 64 wt-% |
| Li$_2$O | 17 to 20 wt-% |
| ZrO$_2$ | 5 to 30 wt-% |
| P$_2$O$_5$ | 1 to 10 wt-% |
| Al$_2$O$_3$ | 0 to 8 wt-% |
| K$_2$O | 0 to 8 wt-% |
| additives | 0 to 5 wt-% |

| Composition 21 | |
|---|---|
| SiO$_2$ | 55 to 64 wt-% |
| Li$_2$O | 10 to 25 wt-% |
| ZrO$_2$ | 8 to 20 wt-% |
| P$_2$O$_5$ | 1 to 10 wt-% |
| Al$_2$O$_3$ | 0 to 8 wt-% |
| K$_2$O | 0 to 8 wt-% |
| additives | 0 to 5 wt-% |

| Composition 22 | |
|---|---|
| SiO$_2$ | 55 to 64 wt-% |
| Li$_2$O | 10 to 25 wt-% |
| ZrO$_2$ | 8 to 15 wt-% |
| P$_2$O$_5$ | 1 to 10 wt-% |
| Al$_2$O$_3$ | 0 to 8 wt-% |
| K$_2$O | 0 to 8 wt-% |
| additives | 0 to 5 wt-% |

| Composition 23 | |
|---|---|
| SiO$_2$ | 55 to 64 wt-% |
| Li$_2$O | 10 to 25 wt-% |
| ZrO$_2$ | 5 to 30 wt-% |
| P$_2$O$_5$ | 1 to 10 wt-% |
| Al$_2$O$_3$ | 0.1 to 5 wt-% |
| K$_2$O | 0 to 8 wt-% |
| additives | 0 to 5 wt-% |

| Composition 24 | |
|---|---|
| SiO$_2$ | 55 to 64 wt-% |
| Li$_2$O | 10 to 25 wt-% |
| ZrO$_2$ | 8 to 20 wt-% |
| P$_2$O$_5$ | 1 to 10 wt-% |
| Al$_2$O$_3$ | 1 to 3 wt-% |
| K$_2$O | 0 to 8 wt-% |
| additives | 0 to 5 wt-% |

| Composition 25 | |
|---|---|
| SiO$_2$ | 55 to 64 wt-% |
| Li$_2$O | 10 to 25 wt-% |
| ZrO$_2$ | 8 to 20 wt-% |
| P$_2$O$_5$ | 1 to 10 wt-% |
| Al$_2$O$_3$ | 0 to 8 wt-% |
| K$_2$O | 0.1 to 5 wt-% |
| additives | 0 to 5 wt-% |

| Composition 26 | |
|---|---|
| SiO$_2$ | 55 to 64 wt-% |
| Li$_2$O | 10 to 25 wt-% |
| ZrO$_2$ | 8 to 20 wt-% |
| P$_2$O$_5$ | 1 to 10 wt-% |
| Al$_2$O$_3$ | 0 to 8 wt-% |
| K$_2$O | 1 to 3 wt-% |
| additives | 0 to 5 wt-% |

The subject according to the application is intended to be explained in more detail with reference to the subsequent figures and examples without restricting said subject to these variants.

DETAILED DESCRIPTION OF THE INVENTION

Figure 1:
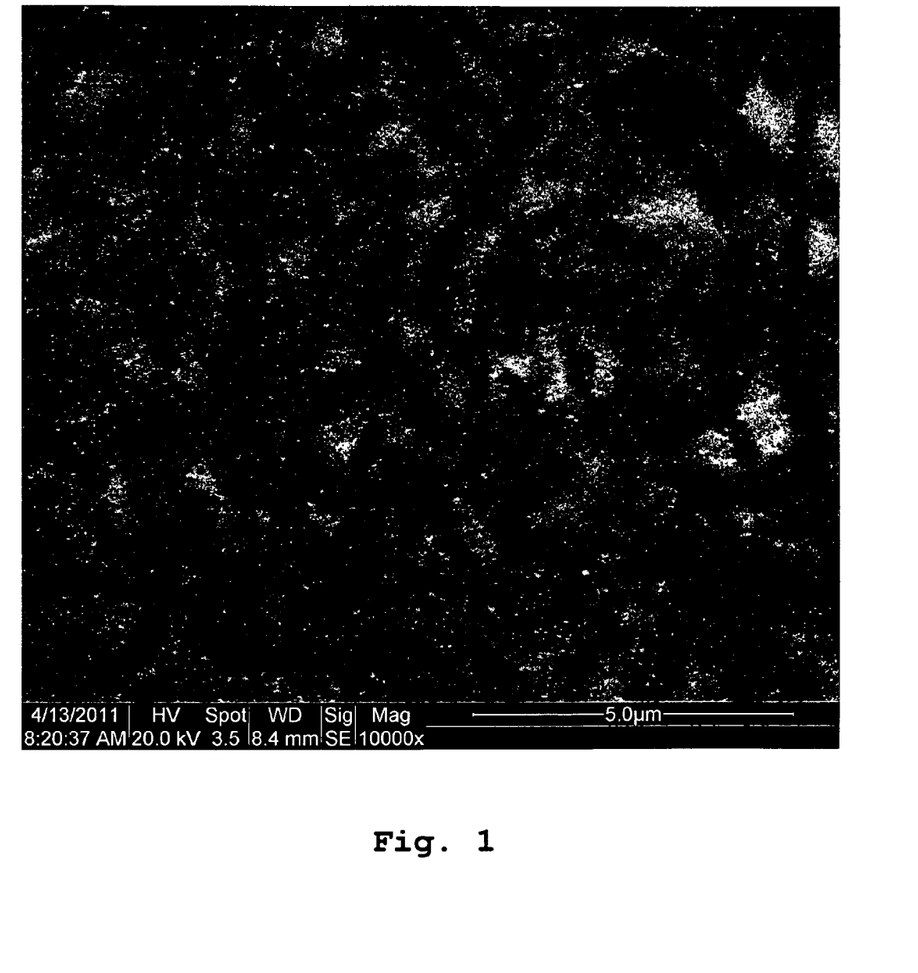
FIG. 1 is a Scanning Electron microscope (SEM) micrograph of a glass ceramic known from the prior art.
Figure 2:
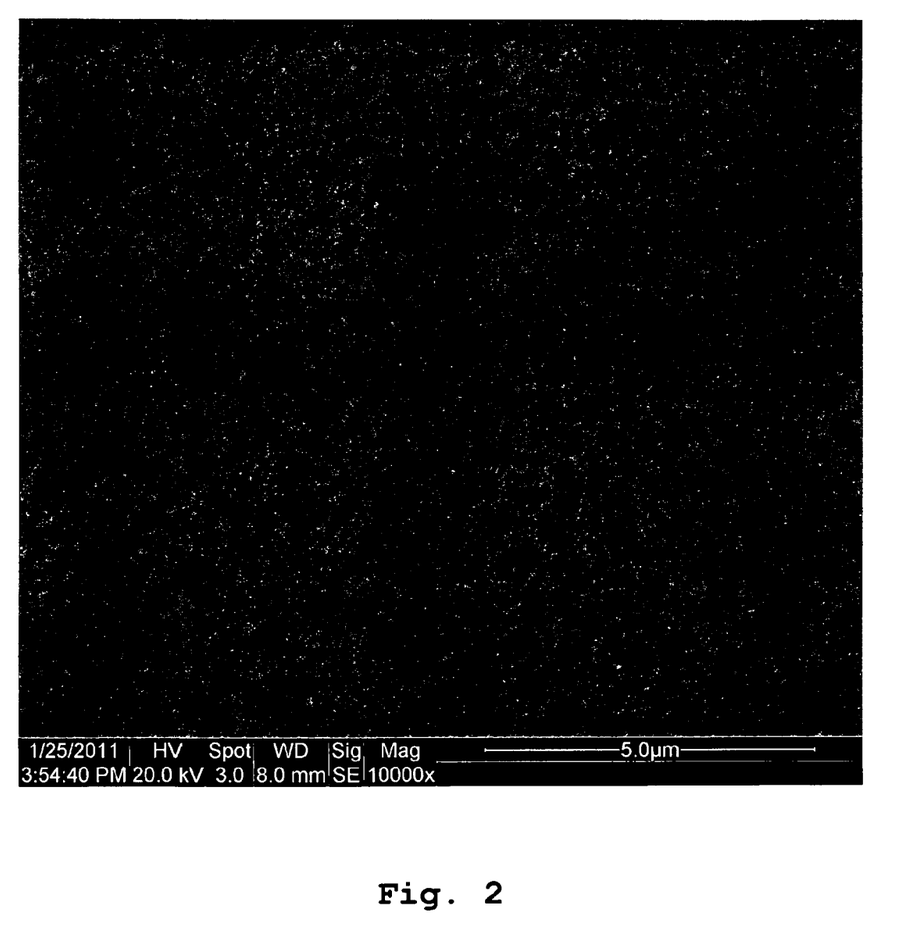
FIG. 2 is a Scanning Electron microscope (SEM) micrograph of a glass ceramic according to the present invention.
Figure 3:
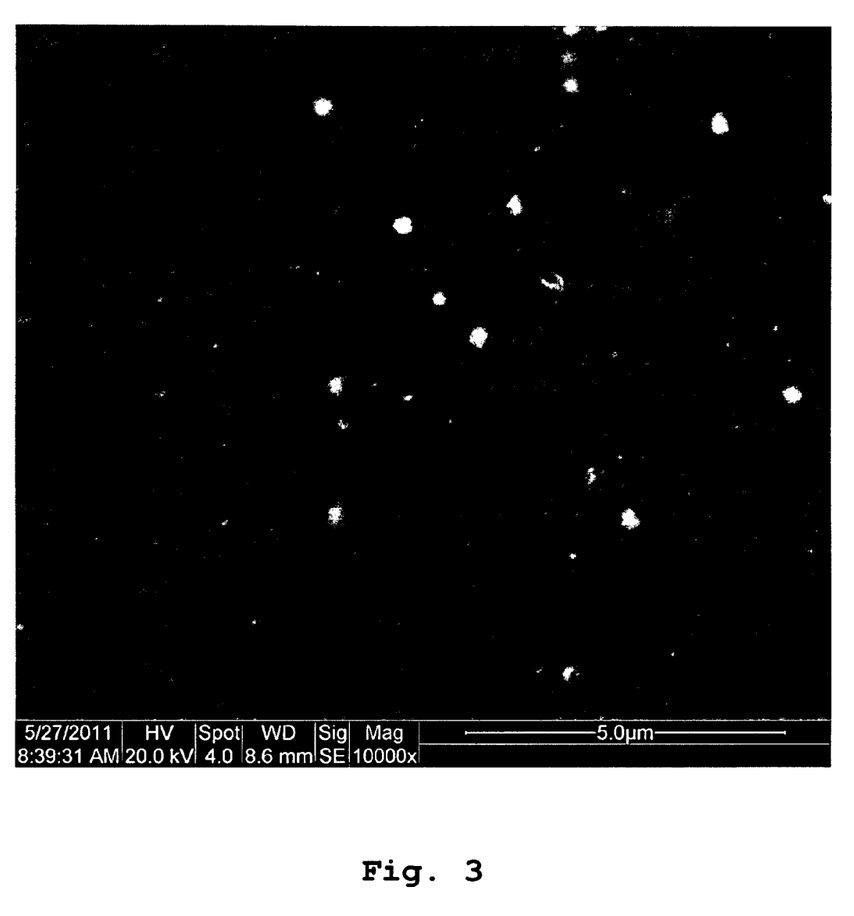
FIG. 3 is a Scanning Electron microscope (SEM) micrograph of a glass ceramic with a low content of stabilizer.

As can be seen from the figures, the glass ceramic according to the present invention shows much better results resulting in a higher translucency as the prior art glass ceramic of FIG. 1.

The glass ceramic of FIG. 3 has a lower amount of stabilizer (4 wt-%) and shows a number of white spots of the stabilizer (ZrO$_2$) which results opaque ceramic which is undesirable in the dental field.

Example 1

In Table 1, compositions which are given by way of example are mentioned, from which high zirconium oxide-containing metasilicate glass ceramics can be produced for the dental field.

TABLE 1

| (Data in % by weight) | | | | | | |
|---|---|---|---|---|---|---|
| | G1 | G2 | G3 | G4 | G5 | G6 |
| SiO$_2$ | 63.5 | 63.5 | 59.0 | 59.0 | 63.5 | 63.5 |
| Li$_2$O | 12.9 | 13.9 | 18.0 | 19.0 | 12.9 | 12.9 |
| ZrO$_2$ | 10.0 | 9.0 | 12.0 | 12.0 | 12.3 | 11.0 |
| Al$_2$O$_3$ | 4.7 | 5.1 | 4.5 | 4.5 | 3.9 | 4.4 |
| P$_2$O$_5$ | 4.5 | 4.5 | 3.5 | 3.5 | 3.7 | 4.2 |
| K$_2$O | 4.4 | 4.0 | 3.0 | 2.0 | 3.6 | 4.0 |

The glasses were melted at 1,500° C. and poured into metal moulds to form blocks. The blocks were stress-relieved in the oven at 560° C. and cooled down slowly. For the various characterisation processes, the glass blocks were divided up and subjected to a first crystallization treatment. For this purpose, the glasses were stored for 10 to 120 minutes at 600° C. to 750° C. As a result of this, glass ceramics with strength values of 150 MPa to 220 MPa (measured according to DIN ISO 6872) were produced. Exclusively lithium metasilicate was hereby established as crystal phase. In this state, processing by means of CAD/CAM methods is possible very readily.

With a second short crystallization at 800° C. to 950° C. for 3 to 15 minutes, the crystallization is continued and the result is an increase in strength from 300 MPa to 450 MPa (measured according to DIN ISO 6872). In addition to the lithium metasilicate phase, a zirconium oxide-containing subsidiary crystal phase can hereby be produced. Also a small conversion of lithium metasilicate into lithium disilicate is possible. The unambiguous main crystal phase remains the lithium metasilicate.

In Table 2, the crystallization conditions of individual glasses and also the resulting crystal phases and strength values are displayed.

TABLE 2

| | Glass | | | | | |
|---|---|---|---|---|---|---|
| | G1 | G2 | G3 | G4 | G5 | G6 |
| 1. Crystallization | 680° C. 10 min | 700° C. 40 min | 690° C. 120 min | 620° C. 120 min | 680° C. 20 min | 700° C. 20 min |
| 2. Crystallization | 820° C. 15 min | 850° C. 10 min | 870° C. 10 min | 880° C. 8 min | 830° C. 15 min | 830° C. 10 min |
| Crystal phases | | | | | | |
| main phase (>80%) | metasilicate | metasilicate | metasilicate | metasilicate | metasilicate | metasilicate |
| subsidiary phase (<20%) | — | — | $ZrO_2$-containing | $ZrO_2$-containing | disilicate | disilicate |
| Translucence | excellent | excellent | very good | very good | excellent | excellent |
| 3-point bending strength | 322 MPa | 418 MPa | 430 MPa | 323 MPa | 403 MPa | 402 MPa |

EXAMPLE 2

In Table 3, fixed compositions given by way of example for different stabilizer is mentioned, from which high stabilizer-containing metasilicate glass ceramics can be produced for the dental field.

TABLE 3

| | in % by weight |
|---|---|
| $SiO_2$ | 60.0 |
| $Li_2O$ | 19.0 |
| $P_2O_5$ | 6.0 |
| $Al_2O_3$ | 2.0 |
| $K_2O$ | 2.0 |
| $CeO_2$ | 1.0 |
| Stabilizer SX* | 10.0 |

*SX represent compositions of the stabilizer S1 to S5 (s. table 4)

Table 4 shows stabilizers used by way of example for dental applications with the composition of table 1.

TABLE 4

| Stabilizers SX | |
|---|---|
| S1 | Zirconium oxide: 10% |
| S2 | Germanium oxide: 10% |
| S3 | Lanthanum oxide: 10% |
| S4 | Yttrium oxide: 10% |
| S5 | Zirconium oxide: 6% |
| | Titanium oxide: 4% |

The glasses were melted at 1,500° C. and poured into metal moulds to form blocks. The blocks were stress-relieved in the oven at 560° C. and cooled down slowly. For the various characterisation processes, the glass blocks were divided up and subjected to a first crystallization treatment. For this purpose, the glasses were stored for 10 to 120 minutes at 600° C. to 750° C. As a result of this, glass ceramics with strength values of 150 MPa to 220 MPa were produced. Exclusively lithium metasilicate was hereby established as crystal phase. In this state, processing by means of CAD/CAM methods is possible very readily.

With a second short crystallization at 800° C. to 950° C. for 3 to 15 minutes, the crystallization is continued and the result is an increase in strength from 300 MPa to 450 MPa. In addition to the lithium metasilicate phase, a zirconium oxide-containing subsidiary crystal phase can hereby be produced. Also a small conversion of lithium metasilicate into lithium disilicate is possible. The unambiguous main crystal phase remains the lithium metasilicate.

In Table 5, the crystallization conditions of individual glasses and also the resulting crystal phases and strength values are shown for different stabilizers.

TABLE 5

| | S1 | S2 | S3 | S4 | S5 |
|---|---|---|---|---|---|
| Crystallization 1 | 620° C./60 min | 540° C./60 min | 615° C./60 min | 620° C./60 min | 620° C./60 min |
| Crystallization 2 | 850° C./8 min | 820° C./8 min | 800° C./8 min | 820° C./8 min | 820° C./8 min |
| Crystal phases | | | Li-metasilicate, (Li-disilicate, Li-phosphate) | | |
| Translucency | exellent | very good | very good | exellent | Good |
| 3-point-bending strength | 418 MPa | 341 MPa | 325 MPa | 363 MPa | 358 MPa |

The invention claimed is:

1. A lithium silicate glass ceramic having the following composition:
   50 to 70 wt-% $SiO_2$,
   17 to 25 wt-% $Li_2O$,
   8 to 20 wt-% of a stabilizer selected from $ZrO_2$ and/or $HfO_2$,
   0.1 to 4 wt-% $K_2O$ and/or $Na_2O$,
   0.1 to 4 wt-% $Al_2O_3$, and
   2 to 8 wt-% additives.

2. The glass ceramic of claim 1 with the following composition:
   50 to 64 wt-% $SiO_2$,
   17 to 20 wt-% $Li_2O$,
   8 to 20 wt-% of a stabilizer selected from $ZrO_2$ and/or $HfO_2$,
   1 to 3 wt-% $K_2O$ and/or $Na_2O$,
   1 to 3 wt-% $Al_2O_3$, and
   4 to 6 wt-% additives.

3. The glass ceramic of claim 1, wherein the stabilizer has substantially an amorphous structure.

4. The glass ceramic of claim 1, wherein the additives are selected from nucleating agents, fluorescent agents, dyes, glass coloring oxides, colored pigments, and mixtures thereof.

5. The glass ceramic of claim 4, wherein the nucleating agents are selected from phosphorous oxide, titanium oxide, tin oxide, noble metals, and mixtures thereof.

6. The glass ceramic of claim 4, wherein the fluorescent agents are selected from oxides of neodymium, praseodymium, samarium, europium, terbium, dysprosium, holmium, erbium, and mixtures thereof.

7. The glass ceramic of claim 4, wherein the glass coloring oxides are selected from oxides of iron, titanium, cerium, copper, chromium, cobalt, nickel, manganese, selenium, silver, indium, gold, vanadium, neodymium, praseodymium, samarium, europium, terbium, dysprosium, holmium, erbium, yttrium, and mixtures thereof.

8. The glass ceramic of claim 1, wherein the additives are selected from boron oxide, fluorine, barium oxide, strontium oxide, magnesium oxide, zinc oxide, calcium oxide, yttrium oxide, titanium oxide, niobium oxide, tantalum oxide, lanthanum oxide and mixtures thereof.

9. A method for producing a dental restoration comprising the glass ceramic of claim 1, wherein
   a) a glass is provided as starting material which comprises the components of the glass ceramic,
   b) the glass is subjected to a first heat treatment for producing a glass ceramic which comprises lithium metasilicate as exclusive or main crystal phase, and
   c) the glass ceramic of b) is subjected to a second heat treatment,
   wherein further metasilicate is segregated from the glass phase and is existent as main crystal phase,
   wherein the first heat treatment is effected with temperatures from 620° C. to 950° C. over a period of 1 to 200 min and/or the second heat treatment is effected with temperatures from 800° C. to 1040° C. over a period of 5 to 200 min.

10. A dental material or a component of a dental material comprising the glass ceramic of claim 1.

11. A shaped dental product comprising a lithium silicate glass ceramic of claim 1.

12. The glass ceramic of claim 5, wherein the nucleating agent is present in an amount of 1 to 10 wt-%.

13. The glass ceramic of claim 6, wherein the fluorescent agent is present in an amount of 0.1 to 5 wt-%.

14. The glass ceramic of claim 7, wherein the glass coloring oxide is present in an amount of 0.1 to 6 wt-%.

15. The glass ceramic of claim 8, wherein the additive is present in an amount of 0.1 to 5 wt-%.

16. The shaped dental product of claim 11, which is an inlay, an onlay, a bridge, an abutment, a facing, a veneer, a facet, a crown, a partial crown, a framework or a coping.

* * * * *